United States Patent [19]
Beitone et al.

[11] Patent Number: 5,653,963
[45] Date of Patent: Aug. 5, 1997

[54] AEROSOL SYSTEM FOR HAIR LACQUER

[75] Inventors: Régis Beitone, Paris; Nicole Konig, Villebon sur Yvette; Veronique Toebat; Jean-Francois Benoist, both of Paris, all of France

[73] Assignee: L'Oreal, Paris, France

[21] Appl. No.: 363,908

[22] Filed: Dec. 27, 1994

Related U.S. Application Data

[63] Continuation of Ser. No. 988,259, Dec. 14, 1992, abandoned

[30] Foreign Application Priority Data

Dec. 13, 1991 [FR] France ................................ 91 1554

[51] Int. Cl.⁶ ........................................................ A61K 7/06
[52] U.S. Cl. .................. 424/47; 424/45; 424/DIG. 1; 424/DIG. 2; 424/70.11; 424/70.9; 424/70.12; 424/70.16; 514/957; 239/573
[58] Field of Search ......................... 424/47, DIG. 1, 424/DIG. 2, 70.1, 70.2, 45, 70.11, 70.12, 70.16, 70.9; 514/957; 239/573

[56] References Cited

U.S. PATENT DOCUMENTS

| | | | |
|---|---|---|---|
| 5,053,218 | 10/1991 | Shernou | 424/47 |
| 5,068,099 | 11/1991 | Sramek | 222/321 |
| 5,085,859 | 2/1992 | Halloran et al. | 424/70.11 |

FOREIGN PATENT DOCUMENTS

| | | |
|---|---|---|
| 0062002 | 10/1982 | European Pat. Off. . |
| 0257444 | 3/1988 | European Pat. Off. . |
| 0455081 | 11/1991 | European Pat. Off. . |
| 2382637 | 9/1978 | France . |
| 2413596 | 7/1979 | France . |
| 2011548 | 7/1979 | United Kingdom . |

OTHER PUBLICATIONS

Berkhout, H. (1991). *Spray Technology & Marketing* May Issue, pp. 36–39.
Gennaro, A.R. (1985). Remington's Pharmaceutical Sciences. Mack Pub. Co., pp. 1670–1672.
Chemical Abstracts (1982). vol. 96, No. 22, Abstract 187093E.
Oteri, R. et al., (1991). Cosmetics & Toiletries. vol. 106, pp. 29–34.

*Primary Examiner*—Raj Bawa
*Attorney, Agent, or Firm*—Cushman Darby & Cushman Intellectual Property Group of Pillsbury Madison & Sutro LLP

[57] ABSTRACT

An aerosol system for dispensing a hair lacquer having a flammability classification less than or equal to 4 according to the Roth apparatus comprises, in combination, an aerosol recipient provided with a value equipped with a dispenser wherein the valve and dispenser have orifices such that the initial outflow of the hair lacquer is between 0.5 and 0.7 g/s. The aerosol recipient contains a hair lacquer composition consisting of 12 to 25% by weight of water, 10 to 26% by weight of an alcoholic phase selected from the group consisting of ethanol, isopropanol and mixtures thereof, and 49 to 78% by weight of dimethyl ether, the alcoholic phase containing from 3 to 5% by weight, compared to the total weight of the composition, of a synthetic film-forming resin.

16 Claims, 1 Drawing Sheet

AEROSOL SYSTEM FOR HAIR LACQUER

This is a continuation of application Ser. No. 07/988,259, filed Dec. 14, 1992, now abandoned.

FIELD OF THE INVENTION

The present invention relates to an aerosol system for dispensing a hair lacquer having the particular characteristic of very low flammability while allowing one to impart excellent lacquering strength to the hair.

BACKGROUND OF THE INVENTION

In the past, hair spray propellents consisted essentially of chlorofluorcarbons which had the enormous advantage of not being flammable but which were presumed to have a harmful effect on the ozone layer.

These chlorofluorocarbon (CFC) propellents, better known as "Freons", have been replaced by hydrocarbons which present fewer risks for the ozone layer, such as propane, n-butane; isobutane or their mixtures.

Nonetheless, these hydrocarbons are currently the subject of very serious criticisms, not only concerning hairsprays but also other cosmetic or domestic products because of their very high flammability.

It has also been proposed to use dimethylether or DME which has the advantage of not being toxic, nor dangerous to the environment and which is partially soluble in water which makes it possible to reduce its flammability.

It has however been noted that aerosol systems for hair sprays containing a mixture of water, alcohol and dimethylether, present certain flammability risks when a high resin content and a satisfactory outflow are desired.

With the aim of avoiding the flammability risks, hairsprays based on dimethylether therefore have only a low resin concentration and a relatively low outflow.

DESCRIPTION OF THE INVENTION

After some research, it has surprisingly been discovered that it is possible to obtain an aerosol system for dispensing a hair lacquer having low flammability and a good lacquering strength, this last factor resulting not only from the resin concentration but also from the outflow of the aerosol system, by using in specifically determined proportions a mixture of water, alcohol and dimethylether, and by using an appropriate valve and dispensing system.

The present invention therefore provides an aerosol system for applying hair lacquer of flammability classification less than or equal to 4 according to the Roth apparatus, comprising in combination an aerosol recipient provided with a valve equipped with a dispenser characterized by the fact that the aerosol recipient contains a composition consisting of:

12 to 25% by weight of water 10 to 26% by weight of an alcoholic phase and 49 to 78% by weight of dimethylether, said alcoholic phase containing a film-forming resin in a proportion of 3 to 6% by weight compared to the total weight of the composition and by the fact that the valve and the dispenser have orifices such that the initial outflow of the hairspray is between 0.5 and 0.7 g/s.

Various studies undertaken according to the Flame Projection Test method with the Roth apparatus confirm that the aerosol system according to the invention is in class 4 or less. According to the Roth test, class 4 corresponds to a flame length greater than 25 cm, without return of the flame and without persistence after the extinction of the igniting flame as is described in French patent 77.39667 (2,413,596) incorporated herein by reference.

Furthermore, the hairsprays according to the invention have been tested for their cosmetic properties and it has been noted that they have an excellent lacquering strength and do not produce any stickiness after drying.

According to a particular embodiment, the composition preferably consists of:

15 to 20% by weight of water, 20 to 25% by weight of alcoholic phase as defined above, and 55 to 65% by weight of dimethylether.

Among particular film-forming resins useable according to the invention are:

vinyl acetate/vinyl tert-butylbenzoate/crotonic acid terpolymers as described in French patent No. 78.30596 (2,439,798) incorporated herein by reference, N-octylacrylamide/methyl methacrylate/hydroxypropyl methacrylate/acrylic acid/tert-butylaminoethyl methacrylate copolymer sold by National Starch under the name AMPHOMER, LV-71®, vinylpyrrolidone/vinyl acetate copolymer sold by BASF under the name LUVISKOL VA 64 POWDER®, vinyl acetate/crotonic acid/vinyl neodecanoate terpolymer sold by National Starch under the name RESINE 28.29.30®.

acrylic acid/ethyl acrylate/N-tert-butylacrylamide terpolymer sold by BASF under the ULTRAHOLD 8®, vinyl acetate/crotonic acid (90/10) copolymer sold by BASF under the name LUVISET CA 66®, vinylcaprolactam/vinylpyrrolidone/dimethylaminoethyl methacrylate copolymer sold by GAF under the name POLYMER ACP-1018®.

According to a particular embodiment, a mixture of film-forming resins may be used.

Among the resins listed above, it is preferred according to the invention to use those described in French patent 78.30596 (2,439,798) and vinyl acetate/crotonic acid/vinyl neodecanoate terpolymer RESINE 28.29.30®).

Those of the above copolymers which include acrylic acid or crotonic acid units are generally used in a form which is partially or totally neutralized using sodium or potassium hydroxide or using an alkanolamine such as 2-amino-2-methyl-propan-1-ol (AMP).

The alcohol of the alcoholic phase is ethanol or isopropanol or a mixture of these, but preferably ethanol.

The composition as defined above may also contain a plasticizer. Among preferred plasticizers are in particular glycol ethers, benzyl alcohol, triethyl citrate, 1,3-butyleneglycol and propylene carbonate.

The composition may also contain other conventional ingredients such as corrosion inhibitors, softeners, perfumes, silicones, sunlight filters, colorants, preservatives, antifoaming agents, vitamins as well as proteins.

The valves used in the aerosol system according to the invention can Be of various structures, the only condition being that the initial outflow of the composition be between 0.5 and 0.7 g/s.

Among the types of valves which may be used are in particular those described in French patent 78.05881 (2,382,637) which is incorporated herein by reference. The equivalent U.S. Pat. No. is No. 4,396,152. This reference describes a valve comprising separate individual conduits for the liquid products and for the gaseous fluid propellent communicating with an impact mixing chamber of the Venturi ejector type into which the unobstructed streams of products and fluid propellent are introduced where they collide and mix to form a fine dispersion which is discharged through an orifice; and dispensing elements simultaneously operable by a single actuator controlling each stream or mixture of streams.

Figure 1:
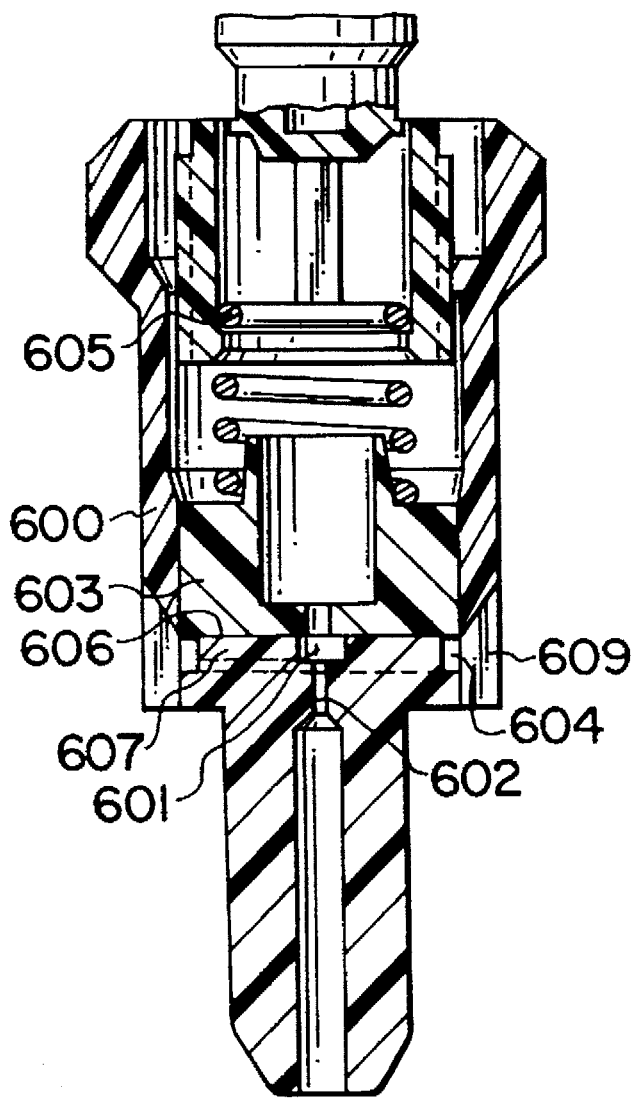
FIG. 1 is a view in elevation, partly cut away of an aerosol dispensor system (FIG. 17 of U.S. Pat. No. 4,396,152)

Among the valves described in this French patent, it is preferred according to the invention to use the one shown in FIG. 17, included herewith as FIG. 1.

These valves have the following characteristics:

valve stem: at least one orifice between 0.40 and 0.60 mm and preferably 2 orifices of 0.50 mm, nozzle orifice between 0.5 and 1 mm (labelled 601 in FIG. 17 of FR 78 05881), internal constriction of the body of the valve (labelled 602 in FIG. 17 of FR 78 05881) between 0.5 and 1 mm, Disc element with two channels (labelled 604 in FIG. 17 of FR 7805881) of dimensions between 0.25×0.25 and preferably 0.25×0.34 mm.

In the valve of FIG. 1, the impact mixing chamber 601 is disposed inside the housing 600. The housing has a central aperture 602 with a venturi constriction for product feed into the chamber 601. The chamber and its feed passages are defined by the bottom wall 606 of the housing and a disclike member 603 abutting the bottom wall of the housing. The bottom wall 606 is cut out to form the mixing chamber 601 transverse passages 607 and an annular recess 604. Openings 609 for feeding the gas propellant to the annular recess and thence to the transverse passages are in the bottom wall outside the product feed passage 602. A spring 605 is positioned atop the disc member against the inner bottom wall of the housing.

Other valves include the "Standard Valve" described in the Aerosol Handbook 2nd Edition (1982), page 170, FIG. 5, having valve stem orifices between 0.33 and 0.60 mm and an internal constriction of the body of the valve between 0.33 and 1.3 mm.

According to the invention, the dispenser comprises a swirl nozzle whose orifice is between 0.40 and 0.60 mm.

There follows, for illustration purposes and without any limiting character several examples of aerosol systems for hair lacquers.

EXAMPLE 1

An aerosol hairspay is prepared by filling an appropriate aerosol recipient with:

| vinyl acetate/vinyl tertbutylbenzoate/<br>crotonic acid terpolymer (65/25/10 by<br>weight) according to French patent 78.30596 | 6 g |
|---|---|
| AMP | qs for 100%<br>neutralization |
| ethanol | 19 g |
| water | 18 g |

An AQUASOL® valve from Value Precision was affixed and the recipient hermetically sealed and thereafter 57 g of dimethylether were introduced using conventional techniques.

The AQUASOL® valve has the following characteristics:

valve stem: 2 orifices of 0.50 mm nozzle orifice: 1 mm internal constriction of body of valve: 1 mm AQUASOL® nozzle: 2×0.25×0.34 mm channels.

This aerosol system is also provided with an immersion capillary tube and a dispenser with swirl nozzle of 0.5 mm.

This aerosol system provides an outflow of 0.65 g/s and its flammability is in class 4 according to the Roth apparatus.

EXAMPLE 2

An aerosol hair spray is prepared by filling an appropriate aerosol recipient with:

| vinyl acetate/crotonic acid/vinyl neodecanoate<br>terpolymer RESINE 28.29.30 ® by National Starch | 3 g |
|---|---|
| AMP | qs for 100%<br>neutralization |
| ethanol | 22 g |
| water | 15 g |

The valve is fixed and the recipient hermetically sealed and thereafter 65 g of dimethylether are introduced using conventional techniques. The "Standard Valve" used has the following characteristics:

valve stem: 1 orifice 0.4 mm internal constriction of body of valve: 0.33 mm

This aerosol system is equipped with a dispenser with a 0.5 mm swirl nozzle.

This aerosol system provides an outflow of 0.57g/s and its flammability corresponds to class 4 according to the Roth apparatus.

EXAMPLE 3

A hairspray is prepared following the method of example 1, using the same equipment, using:

N-octylacrylamide/methyl methacrylate/hydroxypropyl methacrylate/acrylic acid/tert-butylaminoethyl methacrylate copolymer sold as AMPHOMER LV 71® by National Starch . . . 3 g.

| N-octylacrylamide/methyl methacrylate/hydroxypropyl<br>methacrylate/acrylic acid/tert-butylaminoethyl<br>methacrylate copolymer sold as AMPHOMER LV 71 ®<br>by National Starch | 3 g |
|---|---|
| AMP | qs for 100%<br>neutralization |
| ethanol | 19 g |
| water | 16 g |
| dimethyl ether | 62 g |

This aerosol system gives an outflow of 0.62g/s and its flammability corresponds to class 4 according to the Roth apparatus.

EXAMPLE 4

An aerosol hairspray is prepared in the same way and using the same equipment as for example 2 using:

| vinyl acetate/vinyl tertbutylate/crotonic acid<br>terpolymer (65/25/10 by weight) from<br>French patent 78.30596 | 4 g |
|---|---|
| AMP | qs for 100%<br>neutralization |
| ethanol | 16 g |
| water | 20 g |
| dimethylether | 60 g |

This aerosol system provides an outflow of 0.57 g/s and its flamability corresponds to class 4 according to the Roth apparatus.

We claim:

1. An aerosol system for dispensing hair lacquer comprising, in combination, an aerosol canister provided with a valve equipped with a dispenser, said valve and dispenser having orifices such that the initial outflow of said hair lacquer is between 0.5 and 0.7 g/s, said valve having an internal body constriction between 0.5 and 1 mm, a nozzle orifice between 0.5 and 1 mm, a valve stem having at least one orifice between 0.33 and 0.60 mm and a disc member having two channels of dimensions between 0.25×0.25 and 0.45×0.54, said aerosol canister containing a hair lacquer composition consisting essentially of 12 to 25 weight percent of water, 10 to 26 weight percent of an alcoholic phase selected from the group consisting of ethanol, isopropanol and a mixture thereof, and 49 to 78 weight percent of dimethylether, said alcoholic phase containing 3 to 6 weight percent of a synthetic film-forming resin.

2. The aerosol system of claim 1 wherein said hair lacquer composition contains in said aerosol recipient 15 to 20 weight percent water, 20 to 25 weight percent of said alcoholic phase and 55 to 65 weight percent of said dimethylether.

3. The aerosol system of claim 1 wherein said synthetic film-forming resin is selected from the group consisting of vinyl acetate/vinyl tertiarybutylbenzoate/crotonic acid terpolymer, N-octylacrylamide/methylmethacrylate/hydroxypropyl methacrylate/acrylic acid/tert-butylaminoethyl methacrylate copolymer, vinylpyrrolidone/vinyl acetate copolymer, vinyl acetate/crotonic acid/vinyl neodecanoate terpolymer, acrylic acid/ethyl acrylate/N-tert-butylacrylamide terpolymer, vinyl acetate/crotonic acid polymer, vinylcaprolactam/vinylpyrrolidone/dimethylaminoethylmethacrylate polymer, and a mixture thereof.

4. The aerosol system of claim 3 wherein said synthetic film-forming resin contains acrylic acid or crotonic acid units, said units being neutralized with an agent selected from the group consisting of sodium hydroxide, potassium hydroxide and an alkanolamine.

5. The aerosol system of claim 1 wherein said hair lacquer composition further contains a corrosion inhibitor.

6. The aerosol system of claim 1 wherein said dispenser comprises a swirl nozzle orifice ranging from 0.40 to 0.60 mm.

7. The aerosol system of claim 1 wherein said hair lacquer composition further contains a silicone.

8. The aerosol system of claim 1 wherein said hair lacquer composition further contains a sunlight filter.

9. The aerosol system of claim 1 wherein said hair lacquer composition further contains a colorant.

10. The aerosol system of claim 1 wherein said hair lacquer composition further contains a preservative.

11. The aerosol system of claim 1 wherein said hair lacquer composition further contains an antifoaming agent.

12. The aerosol system of claim 1 wherein said hair lacquer composition further contains a vitamin.

13. The aerosol system of claim 1 wherein said hair lacquer composition further contains a protein.

14. The aerosol system of claim 1, wherein said hair lacquer composition further contains a softener.

15. The aerosol system of claim 1 wherein said hair lacquer composition further contains a plasticizer.

16. The aerosol system of claim 1, wherein said hair lacquer composition further contains a perfume.

* * * * *